United States Patent
Ignatyev et al.

(10) Patent No.: US 7,541,488 B2
(45) Date of Patent: Jun. 2, 2009

(54) PROCESS FOR THE PREPARATION OF MONO- AND BIS(FLUOROALKYL)PHOSPHORANES AND THE CORRESPONDING ACIDS AND PHOSPHATES

(75) Inventors: Nikolai (Mykola) Ignatyev, Duisburg (DE); Urs Welz-Biermann, Heppenheim (DE); Michael Schmidt, Seeheim-Jugenheim (DE); Andriy Kucheryna, Wuppertal (DE); Helge Willner, Mühlheim/Ruhr (DE)

(73) Assignee: Merck Patent GmbH, Darmstadt (DE)

( * ) Notice: Subject to any disclaimer, the term of this patent is extended or adjusted under 35 U.S.C. 154(b) by 372 days.

(21) Appl. No.: 10/579,556

(22) PCT Filed: Oct. 22, 2004

(86) PCT No.: PCT/EP2004/011940

§ 371 (c)(1), (2), (4) Date: May 16, 2006

(87) PCT Pub. No.: WO2005/049628

PCT Pub. Date: Jun. 2, 2005

(65) Prior Publication Data

US 2007/0088176 A1    Apr. 19, 2007

(30) Foreign Application Priority Data

Nov. 17, 2003    (DE) .................................. 103 53 759

(51) Int. Cl.
    C07F 9/22    (2006.01)
(52) U.S. Cl. .............................................. 562/8; 562/26
(58) Field of Classification Search ..................... 562/8, 562/26

See application file for complete search history.

(56) References Cited

U.S. PATENT DOCUMENTS 7,202,379 B2 *  4/2007  Welz-Biermann et al. ...... 562/8

FOREIGN PATENT DOCUMENTS

GB          734187          7/1955

* cited by examiner

*Primary Examiner*—Rei-tsang Shiao
(74) *Attorney, Agent, or Firm*—Millen, White, Zelano, Branigan, P.C.

(57) ABSTRACT

The invention relates to a method for producing mono(fluoroalkyl)phosphoric acids or bis(fluoroalkyl)phosphoric acids, mono(fluoroalkyl)phosphates or bis(fluoroalkyl)phosphates, and the corresponding phosphoranes thereof. The inventive method comprises at least the step of reacting a bis(fluoroalkyl)phosphonic acid, a (fluoroalkyl)phosphonic acid, or a corresponding derivative of said acids with anhydrous hydrogen fluoride.

24 Claims, No Drawings

PROCESS FOR THE PREPARATION OF MONO- AND BIS(FLUOROALKYL)PHOSPHORANES AND THE CORRESPONDING ACIDS AND PHOSPHATES

The present invention relates to a process for the preparation of mono(fluoroalkyl)- or bis(fluoroalkyl)phosphoric acids, mono(fluoroalkyl) or bis(fluoroalkyl) phosphates and the corresponding phosphoranes thereof.

A process known from the prior art for the synthesis of fluoroalkylphosphoranes is based on the electrochemical Simons fluorination (ECF) of alkylphosphines (N. Ignatyev, P. Satori, *J. of Fluorine Chem.*, 103 (2000) 57-61; WO 00/21969) and, owing to the high yields, is particularly suitable for the synthesis of tris(fluoroalkyl)difluorophosphoranes. In the electro-chemical fluorination of dialkylphosphines having short alkyl chains (having less than $C_4$), the yield of the corresponding perfluorinated phosphoranes is significantly lower.

The tris(fluoroalkyl)difluorophosphoranes can be used as starting materials for the synthesis of various phosphates (WO 98/15562, DE 196 41 138, EP 1 127 888) and a novel tris(fluoroalkyl)trifluorophosphoric acid (DE 101 30 940). This acid can be used not only for the synthesis of various salts, but can also be hydrolysed to give the corresponding bis(fluoroalkyl)phosphinic acid (DE 102 169 97). Bis(fluoroalkyl)phosphinic and fluoroalkylphosphonic acid and salts thereof can also be obtained by hydrolysis of tris(fluoroalkyl)difluorophosphoranes (DE 102 169 95).

A process known from the prior art for the preparation of mono(perfluoroalkyl)- and bis(perfluoroalkyl)fluorophosphoranes is furthermore a multistep reaction based on the reaction between phosphorus and perfluoroalkyl halides, which are very expensive (T. Mahmood, J. M. Shreeve, Inorg. Chem., 25 (1986) 3128). This reaction frequently requires high pressures and temperatures.

Trifluoromethylphosphorane is formed in the reaction of $(CF_3)_2Cd$ with $PF_5$ or $PCl_5$ (R. Eujen, R. Haiges, Z. Naturforsch., 53b (1998) 1455). However, tris(trifluoromethyl) phosphorane is preferentially formed in this reaction, while $CF_3PF_4$ and $(CF_3)_2PF_3$ have only been detected by NMR spectroscopy in the reaction mixture. A further disadvantage of this reaction is the use of the unstable donor-free $(CF_3)_2Cd$, which has to be prepared from expensive $CF_3I$ in a number of steps.

Mono(pentafluorophenyl)- and bis(pentafluorophenyl) fluorophosphoranes can be prepared in a multistep reaction, in which the first step is a reaction of pentafluorophenylmagnesium bromide with $PCl_3$ (M. Fild, O. Glemser, I. Hollenberg, Z. Naturforsch., 21b (1966) 920; D. D. Magnelly, G. Tesi, J. U. Lowe, W. E. McQuistion, Inorg. Chem., 5 (1966) 457; R. M. K. Deng, K. B. Dillon, W. S. Sheldrick, J. Chem. Soc. Dalton Trans. 1990, 551) or with $PBr_3$ (A. H. Cowley, R. P. Pinnell, J. Am. Chem. Soc. 88 (1966) 4533; R. Ali, K. B. Dillon, J. Chem. Soc. Dalton Trans. 1990, 2593). The resultant mixture of mono(pentafluorophenyl)- and bis(pentafluorophenyl)chloro- or -bromophosphine can be separated by fractional distillation, and the corresponding fluorophosphoranes are formed by reaction with $Cl_2$ and subsequent reaction with $AsF_3$ or $SbF_3$ (M. Fild, R. Schmutzler, J. Chem. Soc. (A) 1969, 840).

Furthermore, the prior art describes some syntheses of mono(pentafluoroethyl) and bis(pentafluoroethyl) fluorophosphates, but these are all based on very expensive starting materials and therefore cannot be carried out economically (for example N. V. Pavlenko, L. M. Ygupolskii, Zh. Org. Khim. (russ.) 59 (1989) 528; S. S. Chan, C. J. Willis, Can. J. Chem. 46 (1968) 1237; J. Jander, D. Börner, U. Engelhardt, Liebigs Ann. Chem., 726 (1969) 19).

The object of the present invention is to indicate an industrial and economically advantageous process for the preparation of mono(fluoroalkyl) and bis(fluoroalkyl) phosphates and the corresponding phosphoranes thereof which has, in particular, good yields and is simpler and less expensive than the processes known from the prior art.

This object is achieved in accordance with the invention by the characterising features of the main claim and the coordinated claims.

The invention is distinguished by the fact that bis(fluoroalkyl)phosphinic or fluoroalkylphosphonic acid or salts or derivatives thereof form the corresponding fluoroalkylphosphoric acids by simple reaction with anhydrous hydrogen fluoride (HF) with subsequent salt formation or form the fluoroalkyl phosphates directly in good yields. The mono (fluoroalkyl) or bis(fluoroalkyl) phosphates can then be converted into the corresponding phosphoranes by treatment with strong electrophilic reagents or strong Lewis acids.

For the purposes of the present invention, mono(fluoroalkyl) and bis(fluoroalkyl) phosphates are compounds in which the phosphorus carries five or four fluorine atoms in addition to the one or two fluoroalkyl groups. The mono- and bis(fluoroalkyl) phosphates prepared in accordance with the invention are therefore mono(fluoroalkyl) pentafluorophosphates and bis(fluoroalkyl) tetrafluorophosphates. The corresponding phosphoranes prepared in accordance with the invention accordingly contain respectively four or three fluorine atoms which are bonded directly to the phosphorus atom. For the purposes of the present invention, fluoroalkyl groups are straight-chain or branched alkyl or cycloalkyl groups which are fluorinated and which contain no, one, two or three double bonds.

Fluorinated alkyl groups are, for example, difluoromethyl, trifluoromethyl, pentafluoroethyl, pentafluoropropyl, heptafluoropropyl, pentafluorobutyl, heptafluorobutyl, nonafluorobutyl, $C_5H_4F_7$, $C_5H_2F_9$, $C_5F_{11}$, $C_6H_4F_9$, $C_6H_2F_{11}$, $C_6F_{13}$, $C_7H_4F_{11}$, $C_7H_2F_{13}$, $C_7F_{15}$, $C_8H_4F_{13}$, $C_8H_2F_{15}$, $C_8F_{17}$, $C_9H_4C_{15}$, $C_9H_2C_{17}$, $C_9F_{19}$, $C_{10}H_4F_{17}$, $C_{10}H_2F_{19}$, $C_{10}F_{21}$, $C_{11}H_4F_{19}$, $C_{11}H_2F_{21}$, $C_{11}F_{23}$, $C_{12}H_4F_{21}$, $C_{12}H_2F_{23}$ or $C_{12}F_{25}$. Perfluoroalkyl group means that all H atoms of the alkyl group, as described above, have been replaced by F atoms. The fluorinated alkyl groups may furthermore contain one, two or three double bonds, for example correspondingly fluorinated allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$. Fluorinated means that 1 to 4 fluorine atoms in a perfluoroalkyl or perfluorocycloalkyl group have been replaced by hydrogen atoms. Cycloalkyl groups is taken to mean, for example, saturated or partially or fully unsaturated cycloalkyl groups having 3-7 C atoms, such as cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, which are correspondingly fluorinated and which may be substituted by $C_1$- to $C_6$-alkyl groups, where the cycloalkyl group and the cycloalkyl group substituted by $C_1$- to $C_6$-alkyl groups are themselves fluorinated.

The process according to the invention for the preparation of mono- or bis(fluoroalkyl) phosphates and the corresponding phosphoranes thereof thus comprises at least the reaction of a bis(fluoroalkyl)phosphinic acid or a (fluoroalkyl)phosphonic acid or a corresponding derivative of these acids with anhydrous hydrogen fluoride.

The bis(fluoroalkyl)phosphinic acids and the (fluoroalkyl) phosphonic acids and the corresponding derivatives of these acids can be prepared by conventional methods known to the person skilled in the art. These compounds are preferably prepared by hydrolysis of tris(fluoroalkyl)phosphine oxides, tris-, bis- or mono(fluoroalkyl)phosphoranes, tris-, bis- or mono(fluoroalkyl)phosphoric acids or anhydrides or haloanhydrides of bis(fluoroalkyl)phosphinic acids and (fluoroalkyl)phosphonic acids (cf., for example, DE 102 169 97 and DE 102 169 95) or by reaction of these compounds with alcohols or alkoxides or amines. The esters of fluoroalkylphosphonic acids containing double bonds in the carbon chain can be prepared, for example, by reaction of perfluoroolefins with trialkyl phosphites (Knunjanz et al., Dokl. Akad. Nauk. SSR, 129 (1959) 576-577). The corresponding descriptions are hereby incorporated by way of reference and are regarded as part of the disclosure.

Mixtures of two or more bis(fluoroalkyl)phosphinic acids and/or two or more (fluoroalkyl)phosphonic acids and/or two or more corresponding derivatives of these acids can also be used in accordance with the invention. Preferably, only one bis(fluoroalkyl)phosphinic acid or (fluoroalkyl)phosphonic acid or corresponding derivative of these acids is in each case reacted in the process according to the invention.

The bis(fluoroalkyl)phosphinic acids used in accordance with the invention or the corresponding derivatives thereof have two fluoroalkyl groups, as described above, which are identical or different. Preference is given to the use of bis (fluoroalkyl)phosphinic acids or the corresponding derivatives thereof containing identical fluoroalkyl groups in each case.

In a preferred embodiment of the process according to the invention, use is made of a bis(perfluoroalkyl)phosphinic acid or a (perfluoroalkyl)phosphonic acid or a corresponding derivative of these acids in which the perfluoroalkyl groups contain 1 to 20 C atoms and are straight-chain or branched. Particular preference is given to starting materials whose perfluoroalkyl groups have 1 to 12 C atoms, as described above. Very particular preference is given to pentafluoroethyl, nonafluorobutyl or perfluoroprop-1-enyl.

The preferred derivative of bis(fluoroalkyl)phosphinic acid or (fluoroalkyl)phosphonic acid employed for the process according to the invention is a salt with a mono-, di- or trivalent metal cation. The metal cations which are particularly preferred in accordance with the invention are selected from the group $Li^+$, $Na^+$, $K^+$, $Mg^{2+}$, $Ca^{2+}$, $Ba^{2+}$, $Zn^{2+}$, $Cu^{2+}$ or $Al^{3+}$.

Alternatively, the preferred derivative of bis(fluoroalkyl)phosphinic acid or (fluoroalkyl)phosphonic acid employed for the process according to the invention is a salt with a mono- or divalent organic cation. Particular preference is given to organic cations which contain at least one nitrogen atom and/or are cyclic. The organic cations which are very particularly preferred in accordance with the invention are selected from the group tetraalkylammonium, tetraalkylphosphonium, triarylalkylphosphonium, guanidinium, pyrrolidinium, pyridinium, imidazolium, piperazinium or hexamethylenediammonium.

Furthermore, the derivative of bis(fluoroalkyl)phosphinic acid or (fluoroalkyl)phosphonic acid employed for the process according to the invention is a salt with a polycation. This polycation is particularly preferably in accordance with the invention a polyammonium cation, for example protonated polyethylenimines.

Suitable as further preferred derivative for the process according to the invention are the esters of bis(fluoroalkyl) phosphinic acid or (fluoroalkyl)phosphonic acid. The mono (fluoroalkyl)- or bis(fluoroalkyl)phosphoric acids are formed first and can then be converted into the corresponding phosphates by salt formation. Processes for salt formation are adequately known to the person skilled in the art, for example the reaction of phosphoric acid with a chloride, bromide, iodide, methylsulfonate, methylsulfate, perchlorate, tetrafluoroborate, acetate, trifluoromethylcarboxylate, trifluoromethylsulfonate or carbonate, preferably with a chloride, bromide, methylsulfonate or trifluoromethylsulfonate and one of the cations as described above.

A suitable reaction medium for the process according to the invention is a conventional polar solvent known to the person skilled in the art. Alternatively, the process according to the invention can also be carried out without a solvent, i.e. in anhydrous hydrogen fluoride. Without restricting generality, the polar solvent used is particularly preferably dichloromethane, diethyl ether, diethyl carbonate, dioxane or a mixture thereof; immediately after the reaction with anhydrous HF, the solvents used can also be water or alcohols.

The temperature at which the reaction is preferably carried out in accordance with the invention is between $-20°$ C. and $100°$ C. The reaction is particularly preferably carried out at a temperature of $0°$ C. to room temperature.

In a preferred variant of the process according to the invention, a 4- to 100-fold amount of hydrogen fluoride is used, based on the molar amount of the bis(fluoroalkyl)phosphinic acid or the (fluoroalkyl)phosphonic acid or the corresponding derivative of these acids. Particular preference is given to a 5- to 25-fold molar amount of hydrogen fluoride.

In a further embodiment of the process according to the invention, the mono- or bis(fluoroalkyl) phosphate formed after the reaction with hydrogen fluoride is reacted with a strong electrophilic reagent or a strong Lewis acid.

The choice of a suitable electrophilic reagent or Lewis acid presents the person skilled in the art with absolutely no difficulties. The electrophilic reagent or Lewis acid employed in accordance with the invention is particularly preferably $(CH_3)_3SiCl$, $SO_2Cl_2$, $SbF_5$, $AlCl_3$, $VF_5$, $SbCl_5$, $NbF_5$, $AsF_5$, $BiF_5$, $AlF_3$, $TaF_5$ or a mixture thereof.

The process according to the invention is advantageously a one-step process, which can be carried out inexpensively and simply. In addition, the use of expensive reagents can be avoided; thus, for example, HF can be employed instead of $SF_4$ and $AlCl_3$ can be employed instead of $Cl_2+SbF_3$.

The complete disclosure content of all applications, patents and publications mentioned above and below is incorporated into this application by way of reference.

Even without further comments, it is assumed that a person skilled in the art will be able to utilise the above description in the broadest scope. The preferred embodiments and examples should therefore merely be regarded as descriptive disclosure which is absolutely not limiting in any way.

The NMR spectra were measured in solutions in deuterated solvents at $20°$ C. in a Bruker Avance 300 spectrometer with a 5 mm $^1H$/BB broad-band head with deuterium lock. The measurement frequencies of the various nuclei are: $^1H$:

EXAMPLES

Example 1

5.364 g (17.4 mmol) of lithium bis(pentafluoroethyl)phosphinate in 15 cm$^3$ of dry diethyl ether are cooled using an ice bath, and 8.0 g (400 mmol) of hydrogen fluoride (HF) are added. The reaction mixture is stirred at 0° C. for two hours and then poured into 20 cm$^3$ of ice-water. The ethereal phase is separated off and washed three times with 10 cm$^3$ of water. The ethereal solution is dried using magnesium sulfate and investigated using $^1$H and $^{19}$F NMR spectroscopy, which confirms the formation of tetrafluorobis(pentafluoroethyl) phosphoric acid as a complex with diethyl ether.

$^{19}$F NMR (reference: CCl$_3$F—internal standard; solvent: CD$_3$CN film): −72.13 dm ($^1J_{P,F}$=925 Hz; PF$_4$); −82.80 quinm ($^4J_{F,F}$=7.5 Hz; $^3J_{P,F}$=2.4 Hz; 2CF$_3$); −119.06 d,quin,m ($^2J_{P,F}$=104 Hz; $^3J_{F,F}$=9.2 Hz; 2CF$_2$). $^{31}$P NMR (reference: 85% H$_3$PO$_4$ in D$_2$O; solvent: CD$_3$CN): −149.15 quin,quin,m; $^1J_{P,F}$=925 Hz; $^2J_{P,F}$=104 Hz; $^3J_{P,F}$=2.3 Hz.

Example 2

1.329 g (4.3 mmol) of lithium bis(pentafluoroethyl)phosphinate in 10.5 cm$^3$ of dry diethyl carbonate are cooled using an ice bath, and 2.0 g (100 mmol) of hydrogen fluoride (HF) are added. The reaction mixture is stirred at 0° C. for half an hour, and the solvent is then removed at 70° C. (oil bath) under a vacuum of 1.3 Pa. The residue is investigated using $^1$H and $^{19}$F NMR spectroscopy, which confirms the formation of tetrafluorobis(pentafluoroethyl)phosphoric acid as a complex with diethyl carbonate.

$^{19}$F NMR (reference: CCl$_3$F—internal standard; solvent: CD$_3$CN film): −72.44 d,m ($^1J_{P,F}$=925 Hz; PF$_4$); −82.93 quin,m ($^4J_{F,F}$=7.2 Hz; 2CF$_3$); −119.11 d,quin,m (2$J_{P,F}$=104 Hz; $^3J_{F,F}$=9.2 Hz; 2CF$_2$). $^{31}$P NMR (reference: 85% H$_3$PO$_4$ in D$_2$O; solvent: CD$_3$CN): −147.58 quin,quin,m; $^1J_{P,F}$=925 Hz; $^2J_{P,F}$=104 Hz.

Example 3

3.779 g (11.11 mmol) of potassium bis(pentafluoroethyl) phosphinate in 20 cm$^3$ of dry dioxane are cooled using an ice bath, and 5.0 g (249.9 mmol) of hydrogen fluoride (HF) are added. The reaction mixture is stirred at 0° C. for half an hour, and the solvent is then removed at 50° C. (oil bath) under a vacuum of 1.3 Pa. The residue, 4.146 g of a white solid material, is investigated using $^{19}$F NMR spectroscopy, which confirms the formation of potassium tetrafluorobis(pentafluoroethyl)phosphate. The yield of K[(C$_2$F$_5$)$_2$PF$_4$] is 97.2%.

$^{19}$F NMR (reference: CCl$_3$F—internal standard; solvent: CD$_3$CN film): −71.70 d,m ($^1J_{P,F}$=917 Hz; PF$_4$); −82.35 quinm ($^4J_{F,F}$=7.3 Hz; $^3J_{P,F}$=2.4 Hz; 2CF$_3$); −119.28 d,quin,m ($^2J_{P,F}$=101 Hz; $^3J_{F,F}$=9.1 Hz; $^3J_{F,F}$=1.2 Hz; 2CF$_2$).

$^{31}$P NMR (reference: 85% H$_3$PO$_4$ in D$_2$O; solvent: CD$_3$CN): −150.40 quin,quin,m; $^1J_{P,F}$=917 Hz; $^2J_{P,F}$=101 Hz; $^3J_{P,F}$=2.4 Hz.

Example 4

1.048 g (2.43 mmol) of tetraethylammonium bis(pentafluoroethyl)phosphinate are cooled using an ice bath, and 2.5 g (124.9 mmol) of hydrogen fluoride (HF) are added. The reaction mixture is stirred at 0° C. for 15 minutes and then poured into 20 cm$^3$ of ice-water. The precipitate is filtered off, washed twice with 10 cm$^3$ of water and dried in air, giving 1.028 g of a white solid material. $^1$H and $^{19}$F NMR spectroscopy confirm the formation of tetraethylammonium tetrafluorobis(pentafluoroethyl)phosphate. The yield of [[C$_2$H$_5$)$_4$N][(C$_2$F$_5$)$_2$PF$_4$] is 89.0% (melting point 201-202° C.).

$^{19}$F NMR (reference: CCl$_3$F—internal standard; solvent: CD$_3$CN): −71.62 dm (PF$_4$); −82.30 quin,d,t (2CF$_3$); −119.06 d,quin,q (2CF$_2$); $^1J_{P,F}$=916 Hz; $^2J_{P,F}$=101 Hz; $^3J_{P,F}$=2.4 Hz; $^3J_{F,F}$=9.2 Hz; $^3J_{F,F}$=1.1 Hz; $^4J_{F,F}$=7.4 Hz. $^1$H NMR (reference: TMS; solvent: CD$_3$CN): 1.21 t,m (4CH$_3$); 3.16 q (4CH$_2$); $^3J_{H,H}$=7.3 Hz.

$^{31}$P NMR (reference: 85% H$_3$PO$_4$ in D$_2$O; solvent: CD$_3$CN): −150.48 quin,quin,m; $^1J_{P,F}$=916 Hz; $^2J_{P,F}$=101 Hz; $^3J_{P,F}$=2.2 Hz.

Example 5

4.116 g (9.97 mmol) of 1-ethyl-3-methylimidazolium bis (pentafluoroethyl)phosphinate are cooled using an ice bath, and 5.0 g (250 mmol) of hydrogen fluoride (HF) are added. The reaction mixture is stirred at 0° C. for 15 minutes and then poured into 20 cm$^3$ of ice-water. The precipitate is filtered off, washed twice with 10 cm$^3$ of water and dried in air, giving 4.208 g of a white solid material. $^1$H, $^{31}$P and $^{19}$F NMR spectroscopy confirm the formation of 1-ethyl-3-methylimidazolium tetrafluorobis(pentafluoroethyl)phosphate. The yield is 92.0% (melting point 60° C.).

$^{19}$F NMR (reference: CCl$_3$F—internal standard; solvent: CD$_3$CN): −71.40 d,m ($^1J_{P,F}$=914 Hz; PF$_4$); −82.18 quin,d,t ($^4J_{F,F}$=7.4 Hz, $^3J_{P,F}$=2.4 Hz, $^3J_{F,F}$=1 Hz; 2CF$_3$); −118.80 d,quin,q ($^2J_{P,F}$=101 Hz, $^3J_{F,F}$=9.1 Hz; 2CF$_2$).

$^1$H NMR (reference: TMS; solvent: CD$_3$CN): 1.47 t ($^3J_{H,H}$=7.3 Hz; CH$_3$); 3.82 s (CH$_3$); 4.17 q (CH$_2$); 7.32 d,d ($^3J_{H,H}$=2.3 Hz; $^4J_{H,H}$=1.7 Hz 1H); 7.37 d,d (1H); 8.38 brs (1H).

$^{31}$P NMR (reference: 85% H$_3$PO$_4$ in D$_2$O; solvent: CD$_3$CN): −150.36 quin,quin,m; $^1J_{P,F}$=914 Hz, $^2J_{P,F}$=101 Hz.

Example 6

7.079 g (13.29 mmol) of tributylethylphosphonium bis (pentafluoroethyl)phosphinate are cooled using an ice bath, and 10.0 g (500 mmol) of hydrogen fluoride (HF) are added. The reaction mixture is stirred at 0° C. for 15 minutes and then poured into 20 cm$^3$ of ice-water. The precipitate is filtered off, washed twice with 10 cm$^3$ of water and dried in air, giving 7.324 g of a white solid material. $^1$H, $^{31}$P and $^{19}$F NMR spectroscopy confirm the formation of tributylethylphosphonium tetrafluorobis(pentafluoroethyl)phosphate. The yield is 95.0% (melting point 76° C.).

$^{19}$F NMR (reference: CCl$_3$F—internal standard; solvent: CD$_3$CN): −71.40 d,m ($^1J_{P,H}$=914 Hz; PF$_4$); −82.18 quin,d,t ($^4J_{F,F}$=7.2 Hz; $^3J_{P,F}$=2.4 Hz; $^3J_{F,F}$=1 Hz; 2CF$_3$); −118.80 d,quin,q ($^2J_{P,F}$=101 Hz; $^3J_{F,F}$=8.9 Hz; 2CF$_2$).

$^1$H NMR (reference: TMS; solvent: CD$_3$CN): 0.96 t (3CH$_3$); 1.19 d,t ($^3J_{H,P}$=18.2 Hz; $^3J_{H,H}$=7.6 Hz; CH$_3$); 1.39-1.59 m (12H); 1.92-2.16 m (8H).

$^{31}$P NMR (reference: 85% H$_3$PO$_4$ in D$_2$O; solvent: CD$_3$CN): 34.77 m; −150.36 quin,quin,m; $^1J_{P,F}$=914 Hz; $^2J_{P,F}$=101 Hz.

Example 7

0.699 g (1.53 mmol) of 1-ethyl-3-methylimidazolium bis (pentafluoroethyl)tetrafluorophosphate and 0.290 g (2.17 mmol) of aluminium trichloride are mixed with one another in a Teflon flask at room temperature and under a dry nitrogen atmosphere. The mixture becomes viscous, and a slight rise in the temperature is observed. After stirring for two hours, the flask is evacuated (0.1 mbar), and the volatile product is collected in a flask cooled using liquid nitrogen, giving 0.439 g of bis(pentafluoroethyl)trifluorophosphorane. The yield is 88%.

$^{19}$F NMR (reference: CCl$_3$F—internal standard; solvent: CD$_3$CN film): −49.85 d,m ($^1J_{P,F}$=1143 Hz; PF$_4$); −81.09 brs (2CF$_3$); −116.78 d,m ($^2J_{P,F}$=127 Hz; 2CF$_2$).

$^{31}$P NMR (reference: 85% H$_3$PO$_4$ in D$_2$O; solvent: CD$_3$CN): −39.05 q,quin,m $^1J_{P,F}$=1143 Hz; $^2J_{P,F}$=127 Hz.

Example 8

0.883 g (1.53 mmol) of tributylethylphosphonium bis(pentafluoroethyl)tetrafluorophosphate and 0.290 g (2.10 mmol) of aluminium trichloride are mixed with one another in a Teflon flask at room temperature and under a dry nitrogen atmosphere. The mixture becomes viscous, and a slight rise in the temperature is observed; after 30 minutes, the mixture becomes solid. The flask is evacuated (0.1 mbar) and heated until the mixture melts (about 50° C.), and the volatile product is collected in a flask cooled using liquid nitrogen, giving 0.305 g of bis(pentafluoroethyl)trifluorophosphorane. The yield is 61%.

$^{19}$F NMR (reference: CCl$_3$F—internal standard; solvent: CD$_3$CN film): −49.85 d,m ($^1J_{P,F}$=1143 Hz; PF$_4$); −81.09 brs (2CF$_3$); −116.78 d,m ($^2J_{P,F}$=127 Hz; 2CF$_2$).

$^{31}$P NMR (reference: 85% H$_3$PO$_4$ in D$_2$O; solvent: CD$_3$CN): −39.05 q,quin,m $^1J_{P,F}$=1143 Hz; $^2J_{P,F}$=127 Hz.

Example 9

1.35 g (6.228 mmol) of antimony pentafluoride are introduced into a Teflon flask, and 2.40 g (4.164 mmol) of tributylethylphosphonium bis(pentafluoroethyl)tetrafluorophosphate (prepared as described in Example 6) are added while the reaction mixture is stirred using a magnetic stirrer. The mixture becomes liquid and is heated at 100° C. for 30 minutes. The volatile product is condensed in a Teflon trap cooled using a dry ice/ethanol mixture. After the cold trap has been warmed to room temperature, 1.31 g of liquid bis(pentafluoroethyl)trifluorophosphorane are obtained. The yield of (C$_2$F$_5$)$_2$PF$_3$ is 96.5%, based on the tributylethylphosphonium bis(pentafluoroethyl)tetrafluorophosphate. The NMR data agree with those obtained for the compound in Example 8.

The residue in the reaction flask is a viscous liquid—tributylethylphosphonium hexafluoroantimonate as a complex with excess SbF$_5$ (acidic ionic liquid): [(C$_4$H$_9$)$_3$(C$_2$H$_5$)P]$^+$ SbF$_6^-$ 0.50 SbF$_5$.

Example 10

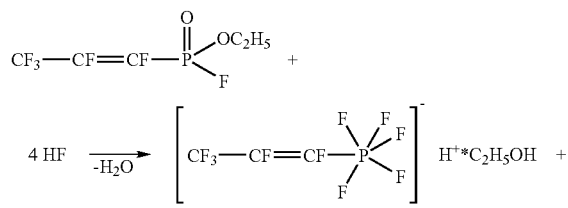

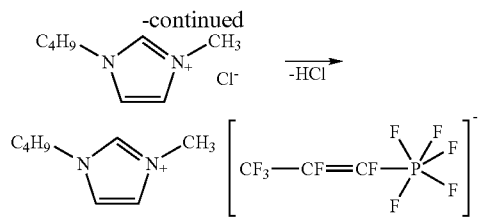

1.023 g (51.15 mmol) of hydrogen fluoride (HF) are cooled to −20° C. using an ethanol bath, and 0.934 g (3.86 mmol) of ethyl perfluoroprop-1-enyl-fluorophosphonate is added. The reaction mixture is stirred at 0° C. The reaction mixture and 0.674 g (3.86 mmol) of 1-butyl-3-methylimidazolium chloride are then mixed with one another at −20° C. in a Teflon flask. After the mixture has been stirred at room temperature for 15 minutes, the flask is evacuated and held for one hour under a reduced pressure of 13.33 Pa and at a bath temperature of 50° C., giving 1.44 g of 1-butyl-3-methylimidazolium perfluoroprop-1-enylpentafluorophosphate. The yield is 94%.

$^{19}$P NMR (reference: CCl$_3$F—internal standard; solvent: CD$_3$CN): −61.39 ddd (4F); $^1J_{F,P}$=784 Hz; $^2J_{F,F}$=48 Hz; $^3J_{F,F}$=14 Hz; −66.72 dd (3F, CF$_3$); $^4J_{F,F}$=23 Hz, $^3J_{F,F}$=11 Hz; −71.51 dquin (1F); $^1J_{F,P}$=731 Hz; 2J$_{F,F}$=48 Hz; −145.2 ddq (1F); $^2J_{F,P}$=100 Hz, $^3J_{F,F}$=132 Hz; $^4J_{F,F}$=23 Hz; −169.5 dm (1F); $^3J_{F,F}$=132 Hz.

$^1$H NMR (reference: TMS; solvent: CD$_3$CN): 0.93 t (3H, CH$_3$); $^3J_{H,H}$=7.4 Hz; 1.32 m (2H, CH$_2$); 1.80 m (2H, CH$_2$); 3.81 s (3H, CH$_3$); 4.11 t (2H, CH$_2$); $^3J_{H,H}$=7.2 Hz; 7.32 m (1H, CH); 7.35 m (1H, CH); 8.42 br.s (1H, CH).

$^{31}$P NMR (reference: 85% H$_3$PO$_4$; solvent: CD$_3$CN): −149.2 dquindd; $^1J_{P,F}$=783 Hz, $^1J_{P,F}$=731 Hz; $^2J_{P,F}$=102 Hz; $^3J_{P,F}$=9 Hz.

NMR spectra of perfluoroprop-1-enylpentafluorophosphoric acid:

$^{19}$F NMR (reference: CCl$_3$F; solvent HF, lock solvent: CD$_3$CN film; −15° C.): −62.1 br.d (5F); $^1J_{P,F}$=684 Hz; −67.73 dd (3F, CF$_3$); $^4J_{F,F}$=23 Hz; $^3J_{F,F}$=11 Hz; −149.3 ddq (1F); $^2J_{F,P}$=109 Hz, $^3J_{F,F}$=133 Hz; $^4J_{F,F}$=23 Hz; −165.8 dm (1F); $^3J_{F,F}$=133 Hz; $^2J_{F,F}$=10 Hz; $^3J_{F,F}$=10 Hz.

$^{31}$P NMR (reference: 85% H$_3$PO$_4$; solvent: HF; lock solvent: CD$_3$CN film; −15° C.): −147.6 br.s.

Example 11

1.2 g of hydrogen fluoride (HF) are cooled using an ice bath, and 0.80 g (2.5 mmol) of methyl bis(pentafluoroethyl) phosphinate, (C$_2$F$_5$)$_2$P(O)OCH$_3$, is added. The reaction mixture is stirred at 0° C. for half an hour. The excess HF is removed by flushing with nitrogen, and the residue is dried under a vacuum of 1.3 Pa, giving 0.87 g of tetrafluorobis(pentafluoroethyl)phosphoric acid, H$^+$[(C$_2$F$_5$)$_2$PF$_4$]$^-$, as a complex with methanol.

$^{19}$F NMR (reference: CCl$_3$F—internal standard; lock: CD$_3$CN film): −73.32 d,m ($^1J_{P,F}$=933 Hz; PF$_4$); −83.97 m (2CF$_3$); −119.68 d,quin ($^2J_{P,F}$=107 Hz; $^3J_{F,F}$=8.3 Hz; 2CF$_2$).

$^1$H NMR (reference: TMS; lock: CD$_3$CN film): 2.86 br.s, 7.27 br.s.

$^{31}$P NMR (reference: 85% H$_3$PO$_4$ in D$_2$O; lock: CD$_3$CN film): −148.8 quin,quin; $^1J_{P,F}$=932 Hz; $^2J_{P,F}$=107 Hz.

The invention claimed is:

1. A process for the preparation of mono(fluoroalkyl)- or bis(fluoroalkyl)phosphoric acid, mono(fluoroalkyl) or bis(fluoroalkyl) phosphates, or the corresponding phosphoranes thereof, comprising:
   reacting a compound which is a bis(fluoroalkyl)phosphinic acid or a salt or ester thereof, or a (fluoroalkyl)phosphonic acid or a salt or ester thereof, with anhydrous hydrogen fluoride,
   wherein said mono(fluoroalkyl) and bis(fluoroalkyl) phosphates are compounds in which the phosphorus carries five or four fluorine atoms in addition to the one or two fluoroalkyl groups,
   said corresponding phosphoranes contain four or three fluorine atoms bonded directly to the phosphorus atom, and
   the fluoroalkyl groups are straight-chain or branched alkyl or cycloalkyl groups which are fluorinated and which contain no double bonds, or one, two or three double bonds, and
   said cycloalkyl groups are saturated, or partially or fully unsaturated, which are optionally substituted by $C_1$- to $C_6$-alkyl groups.

2. A process according to claim 1, wherein said compound is a bis(fluoroalkyl)phosphinic acid or a salt or ester thereof, and said bis(fluoroalkyl)phosphinic acid or a salt or ester thereof has two fluoroalkyl groups are identical or different.

3. A process according to claim 1, wherein said bis(fluoroalkyl)phosphinic acid or salt or ester thereof, or said (fluoroalkyl)phosphonic acid or salt or ester thereof have perfluoroalkyl groups having 1 to 20 C atoms that are straight-chain or branched.

4. A process according to claim 1, wherein said compound is a salt of a bis(fluoroalkyl)phosphinic acid with a mono-, di- or trivalent metal cation or a salt of a (fluoroalkyl)phosphonic acid with a mono-, di- or trivalent metal cation.

5. A process according to claim 4, wherein said mono-, di- or trivalent metal cation is $Li^+$, $Na^+$, $K^+$, $Mg^{2+}$, $Ca^{2+}$, $Ba^{2+}$, $Zn^{2+}$, $Cu^{2+}$ or $Al^{3+}$.

6. A process according to claim 1, wherein said compound is a salt of bis(fluoroalkyl)phosphinic acid with a mono- or divalent organic cation or a salt of (fluoroalkyl)phosphonic acid with a mono- or divalent organic cation.

7. A process according to claim 6, wherein said mono- or divalent organic cation is tetraalkylammonium, tetraalkylphosphonium, triarylalkylphosphonium, guanidinium, pyrrolidinium, pyridinium, imidazolium, piperazinium, or hexamethylenediammonium.

8. A process according to claim 1, wherein said compound is an ester of bis(fluoroalkyl)phosphinic acid or an ester of (fluoroalkyl)phosphinic acid.

9. A process according to claim 1, wherein said compound is a salt of bis(fluoroalkyl)phosphinic acid or (fluoroalkyl)phosphonic acid with a polycation.

10. A process according to claim 9, wherein said polycation is a polyammonium cation.

11. A process according to claim 1, wherein said reaction is carried out in a polar solvent.

12. A process according to claim 1, wherein said reaction is carried out at a temperature of $-20°$ C. to $100°$ C.

13. A process according to claim 1, wherein said reaction is carried out with 4- to 100-fold the molar amount of hydrogen fluoride.

14. A process according to claim 1, wherein said process is for the preparation of phosphoranes, and the mono- or bis(fluoroalkyl) phosphate formed after reaction with hydrogen fluoride is reacted with a strong electrophilic reagent or a strong Lewis acid.

15. A process according to claim 14, wherein said reaction is carried out with an electrophilic reagent or a Lewis acid selected from $(CH_3)_3SiCl$, $SO_2Cl_2$, $SbF_5$, $AlCl_3$, $VF_5$, $SbCl_5$, $NbF_5$, $AsF_5$, $BiF_5$, $AlF_3$ and $TaF_5$.

16. A process according to claim 1, wherein said reaction is carried out without a solvent.

17. A process according to claim 1, wherein said fluoroalkyl groups are in each case selected from
   difluoromethyl, trifluoromethyl, pentafluoroethyl, pentafluoropropyl, heptafluoropropyl, pentafluorobutyl, heptafluorobutyl, nonafluorobutyl, $C_5H_4F_7$, $C_5H_2F_9$, $C_5F_{11}$, $C_6H_4F_9$, $C_6H_2F_{11}$, $C_6F_{13}$, $C_7H_4F_{11}$, $C_7H_2F_{13}$, $C_7F_{15}$, $C_8H_4F_{13}$, $C_8H_2F_{15}$, $C_8F_{17}$, $C_9H_4C_{15}$, $C_9H_2C_{17}$, $C_9F_{19}$, $C_{10}H_4F_{17}$, $C_{10}H_2F_{19}$, $C_{10}F_{21}$, $C_{11}H_4F_{19}$, $C_{11}H_2F_{21}$, $C_{11}F_{23}$, $C_{12}H_4F_{21}$, $C_{12}H_2F_{23}$, $C_{12}F_{25}$,
   fluorinated allyl, 2- butenyl, 3-butenyl, isobutenyl, sec-butenyl, furthermore 4-pentenyl, isopentenyl, hexenyl, heptenyl, octenyl, —$C_9H_{17}$, or —$C_{10}H_{19}$ to —$C_{20}H_{39}$, or
   a fluorinated saturated or partially or fully unsaturated cycloalkyl groups having 3-7 C atoms, optionally substituted by substituted by $C_1$- to $C_6$-alkyl groups.

18. A process according to claim 17, wherein said cycloalkyl groups are selected from fluorinated cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, which are in each case optionally substituted by $C_1$- to $C_6$-alkyl groups.

19. A process according to claim 1, wherein said fluoroalkyl groups are straight-chain or branched perfluoroalkyl groups having 1 to 20 C atoms.

20. A process according to claim 1, wherein said fluoroalkyl groups are straight-chain or branched perfluoroalkyl groups having 1 to 12 C atoms.

21. A process according to claim 20, wherein at least one of said fluoro-alkyl groups is pentafluoroethyl, nonafluorobutyl or perfluoroprop-1-enyl.

22. A process according to claim 1, wherein said reaction is carried out at a temperature of $0°$ C. to room temperature.

23. A process according to claim 1, wherein said reaction is carried out with 5- to 25-fold molar amount of hydrogen fluoride.

24. A process according to claim 1, wherein said compound is:
   lithium bis(pentafluoroethyl)phosphinate,
   potassium bis(pentafluoroethyl)phosphinate,
   tetraethylammonium bis(pentafluoroethyl)phosphinate,
   1-ethyl-3-methylimidazolium bis(pentafluoroethyl)phosphinate,
   tributylethylphosphonium bis(pentafluoroethyl)phosphinate,
   1-ethyl-3-methylimidazolium bis(pentafluoroethyl)tetrafluorophosphate,
   tributylethylphosphonium bis(pentafluoroethyl)tetrafluorophosphate,
   ethyl perfluoroprop-1-enyl-fluorophosphonate, or
   methyl bis(pentafluoroethyl)phosphinate.

* * * * *